US012564465B2

(12) United States Patent
Bedingfield

(10) Patent No.: US 12,564,465 B2
(45) Date of Patent: Mar. 3, 2026

(54) SYSTEMS AND METHODS FOR AN AIRWAY ISOLATION DRAPE APPARATUS

(71) Applicant: Dignity Health, San Francisco, CA (US)

(72) Inventor: Gaylyn Bedingfield, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 484 days.

(21) Appl. No.: 18/004,833

(22) PCT Filed: Jul. 7, 2021

(86) PCT No.: PCT/US2021/040608
§ 371 (c)(1),
(2) Date: Jan. 9, 2023

(87) PCT Pub. No.: WO2022/010961
PCT Pub. Date: Jan. 13, 2022

(65) Prior Publication Data
US 2023/0255715 A1 Aug. 17, 2023

Related U.S. Application Data

(60) Provisional application No. 63/049,519, filed on Jul. 8, 2020, provisional application No. 63/137,001, filed on Jan. 13, 2021.

(51) Int. Cl.
*A61B 46/20* (2016.01)
*A61B 17/00* (2006.01)
(Continued)

(52) U.S. Cl.
CPC .................................... *A61B 46/20* (2016.02)

(58) Field of Classification Search
CPC .............. A61B 17/00; A61B 2046/201; A61B 2046/205; A61B 2017/00907;
(Continued)

(56) References Cited

U.S. PATENT DOCUMENTS 2,915,074 A 12/1959 Cameto
5,014,374 A 5/1991 Williams
(Continued)

OTHER PUBLICATIONS

Patent Cooperation Treaty, International Search Report and Written Opinion, International Application No. PCT/US2021/040608, date of mailing Oct. 20, 2021, 11 pages.

*Primary Examiner* — Alireza Nia
*Assistant Examiner* — Andrew Jun-Wai Mok
(74) *Attorney, Agent, or Firm* — Polsinelli PC

(57) ABSTRACT

Various embodiments for an airway isolation apparatus having a wire frame that is operable for deploying an isolation drape over a subjects head to protect healthcare and other workers from contagious or otherwise harmful agents are disclosed herein. The drape frame may include a frame base. A frame channel may extend from the frame base and a frame wire may extend through the frame channel A frame opening may be defined by the frame base and the frame channel of the drape frame. A drape may be disposed in the frame opening. Accordingly, the drape frame may be deployed in place over the chest and head of a subject. The drape may cover the subjects head to isolate the mouth and nose of the subject preparatory to accessing these airways for intubation or other procedure.

20 Claims, 7 Drawing Sheets

(51) Int. Cl.

| | | |
|---|---|---|
| *A61B 90/00* | (2016.01) |
| *A61B 90/40* | (2016.01) |
| *A61G 10/00* | (2006.01) |

(58) Field of Classification Search
CPC ... A61B 2090/401; A61B 90/40; A61B 46/00;
A61B 46/20; A61G 10/00; A61G 10/04;
A61G 1/04
See application file for complete search history.

(56) References Cited

U.S. PATENT DOCUMENTS

| | | | | |
|---|---|---|---|---|
| 2010/0122414 | A1* | 5/2010 | Shah ................... | A61G 13/122 |
| | | | | 5/637 |
| 2011/0056489 | A1 | 3/2011 | Slaker et al. | |
| 2014/0090680 | A1* | 4/2014 | Reis ...................... | A61G 1/017 |
| | | | | 135/96 |
| 2015/0238264 | A1 | 8/2015 | Kerns et al. | |
| 2016/0220428 | A1 | 8/2016 | Butterfield et al. | |

* cited by examiner

SYSTEMS AND METHODS FOR AN AIRWAY ISOLATION DRAPE APPARATUS

FIELD

The present disclosure relates generally to medical devices, and more particularly, to an airway isolation drape apparatus having a wire frame operable for deploying an isolation drape over the subject's head to protect healthcare and other workers from contagious or otherwise harmful agents.

BACKGROUND

Virus and bacteria pose a serious threat to humankind. A recent, particularly serious example of such a threat has been the worldwide pandemic caused by a strain of coronavirus known as Severe Acute Respiratory Syndrome Coronavirus 2 (SARS-CoV-2). This coronavirus causes a disease known as Covid-19, which has evolved into a global pandemic that has caused over 500,000 deaths worldwide throughout the first half of 2020, as well as a serious threat to the economies of many industrialized countries.

Medical professionals have been strongly hit by Covid-19. For example, in some countries, it is estimated that the Covid-19 death rate among doctors, nurses and other medical professionals may have doubled said death rate among the general population. The main cause of such a death toll within the medical profession has been the lack of sufficient personal protection equipment or PPE, which has caused a high number of medical professionals to become infected with elevated virus loads. Especially during the first months of the pandemic, medical professionals have been required to work face-to-face with Covid-19 subjects, without being provided with proper protective clothing, goggles, or even protective face masks.

Due to the increasing incidence of Covid-19, the world is facing a need for accelerated and massive manufacture of protective equipment for both medical professionals and the general population. In addition, there is an increased need for new protective equipment or devices that can further assist medical personnel and other professionals in combatting the pandemic.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Various embodiments for an airway isolation drape that protects health care workers and others from a contagiously ill subject, such as one suffering from Covid-19, are disclosed herein. In some embodiments, the airway isolation drape may include a transparent or translucent drape. In one aspect, the airway isolation drape may be secured to the subject and/or a surface such as a bed, operating room table, stretcher, etc. while the subject is lying thereon. In some embodiments, the airway isolation drape is secured to a surface by an adhesive, which is operable to attach the airway isolation drape to the chest of the subject, and/or a belt that secures the airway isolation drape to the underside of the operating room table.

Figure 1:
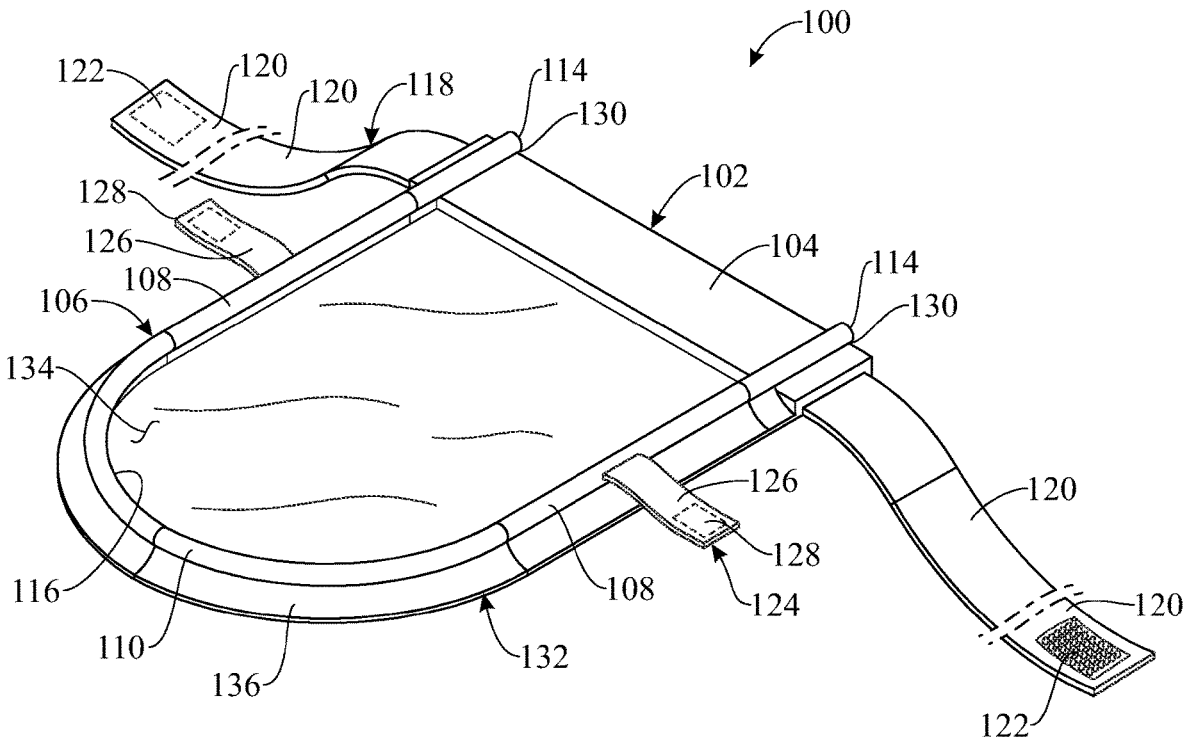
FIG. 1 presents a top perspective view of an airway isolation drape assembly in a horizontal position in accordance with an illustrative embodiment of the present invention.

Referring initially to FIG. 1, an airway isolation drape assembly, hereinafter drape assembly 100, is illustrated in accordance with an illustrative embodiment of the present invention as mentioned heretofore. As will be hereinafter described in greater detail, and shown in FIGS. 4-7, the drape assembly 100 is operable for deployment in place over a chest 142 and face 144 of a subject 140 as the subject 140 lies on a surface 150 such as a stretcher, bed, operating table, or other support surface. The drape assembly 100 may enable medical personnel to access the airways of the subject 140 as the drape assembly 100 protects the personnel from viruses, bacteria and/or other potentially harmful microorganisms which may be ejected from the mouth and/or nose of the subject 140.

It must be noted that, while the present description will use the terms "subject", "medical personnel" and the like in order to refer to medical applications of the invention, the invention may be used in other environments or situations. For instance, the present invention may be used in a home or other living or lodging facility to protect third persons who share the facility with an infected person.

Figure 4:
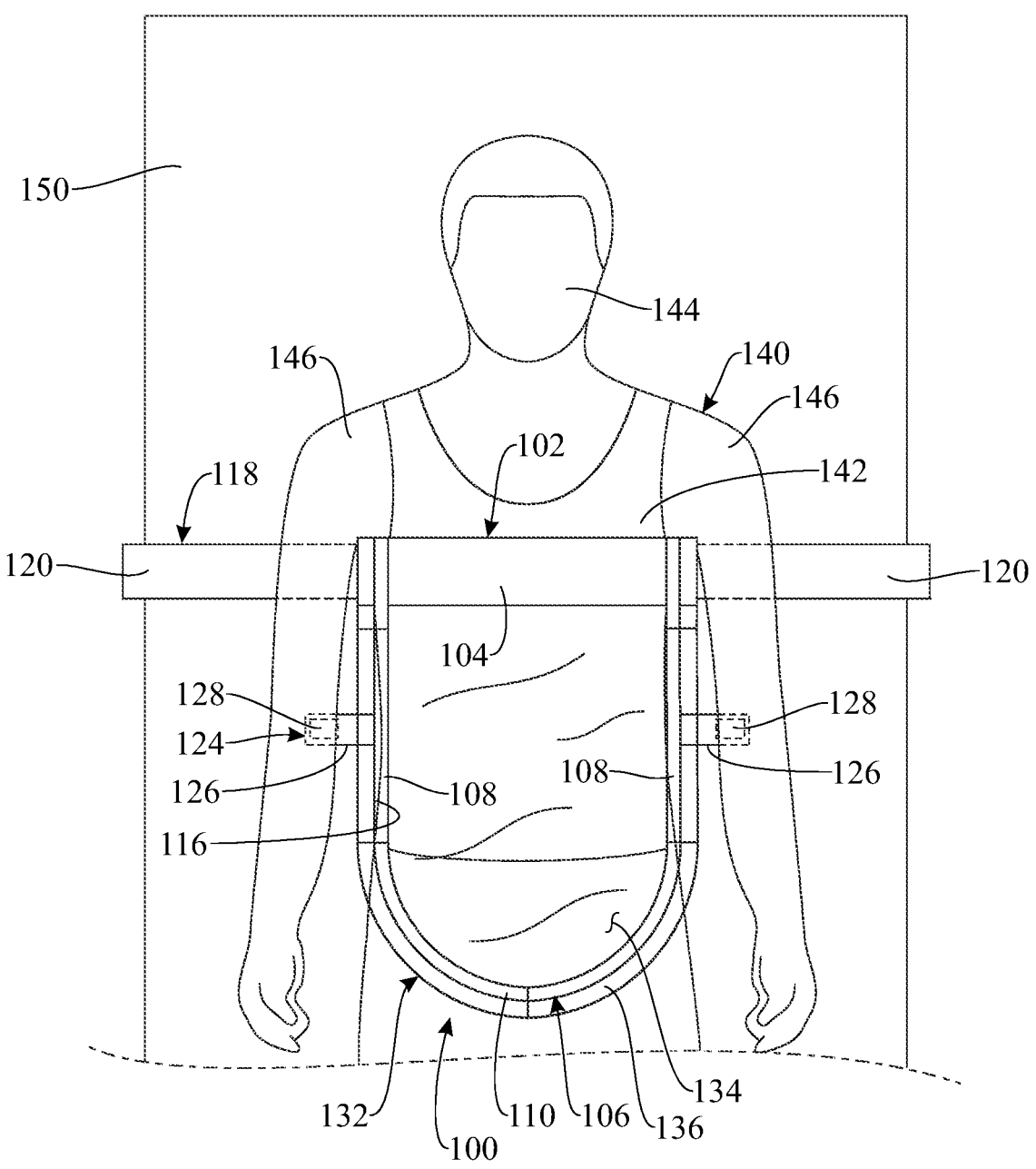
FIG. 4 presents a top view of the airway isolation drape assembly of FIG. 1 over a subject lying on a subject support surface preparatory to deployment of the frame channel and drape over the head of the subject.
Figure 5:
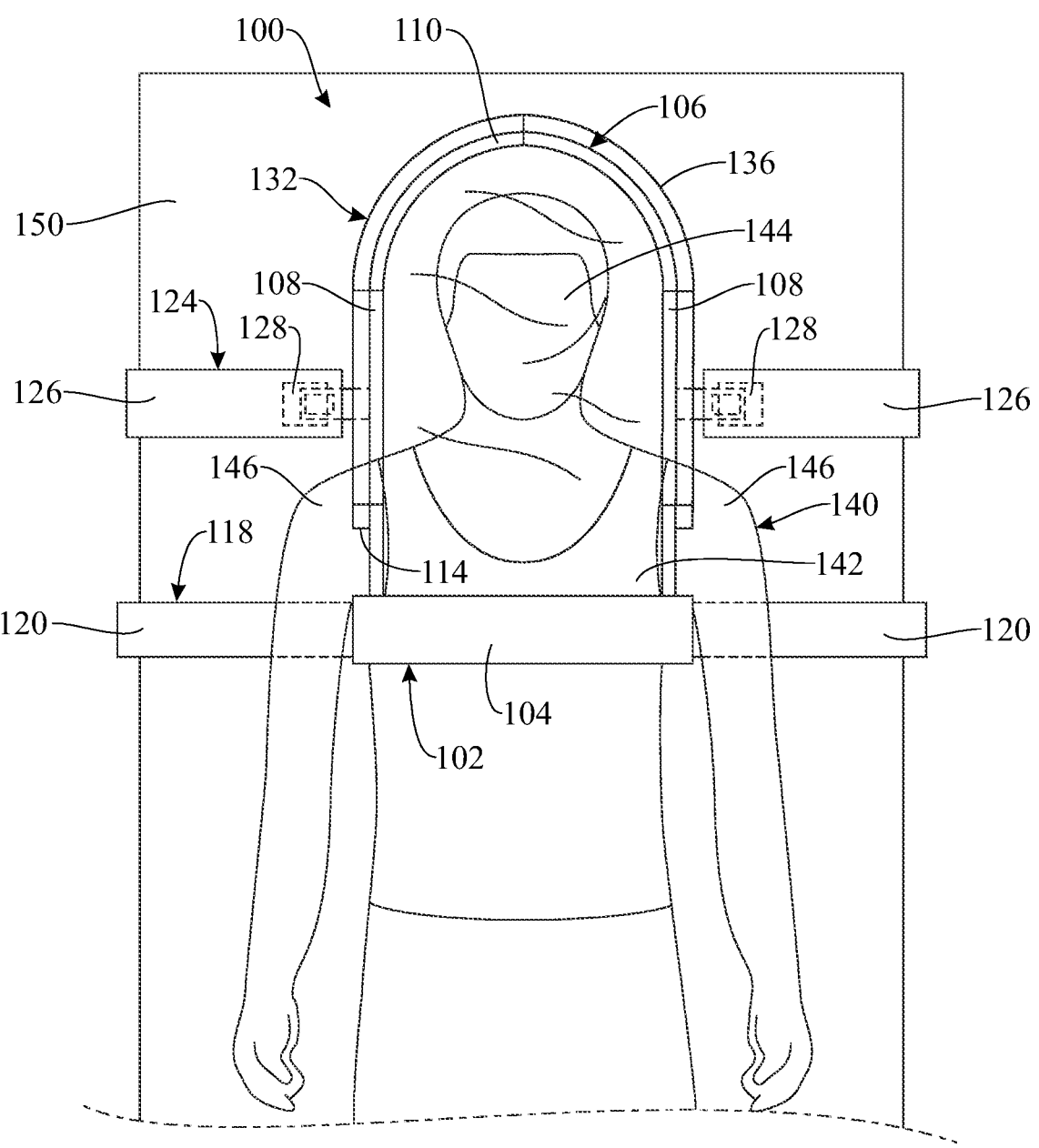
FIG. 5 presents a top view of the airway isolation drape assembly of FIG. 1 with the frame channel and drape deployed in a horizontal position over the head of the subject.

With continued reference to FIG. 1, the drape assembly 100 includes a drape frame 102 including a frame base 104. In some embodiments, the frame base 104 is elongated and configured to extend across a subject's torso, as will be described hereinafter and as illustrated in FIGS. 4 and 5. In some embodiments, such as the present embodiment, the frame base 104 may be of a rectangular shape, however, the frame base 104 can be tubular, rounded, or of an otherwise alternative configuration.

Figure 2:
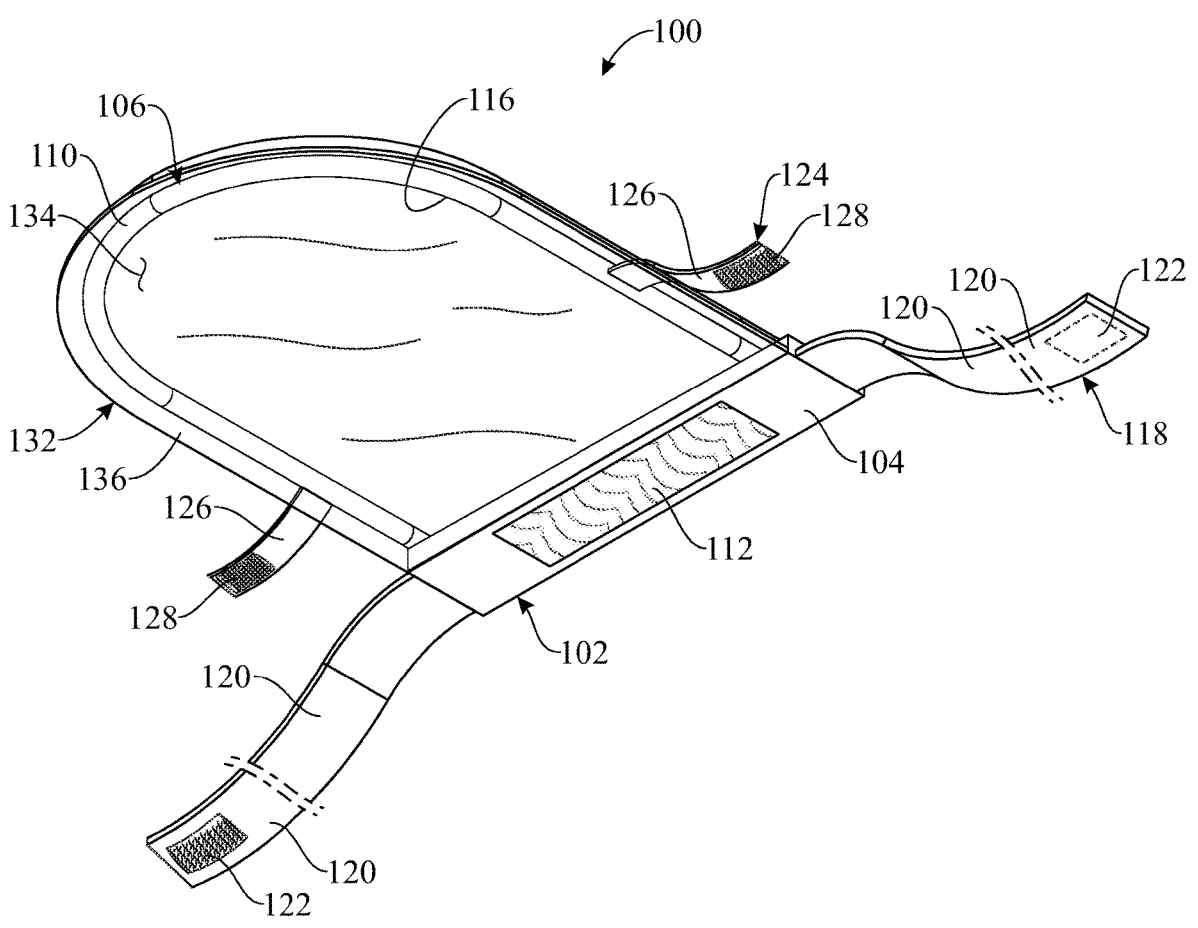
FIG. 2 presents a bottom perspective view of the airway isolation drape assembly illustrated in FIG. 1.
Figure 3:
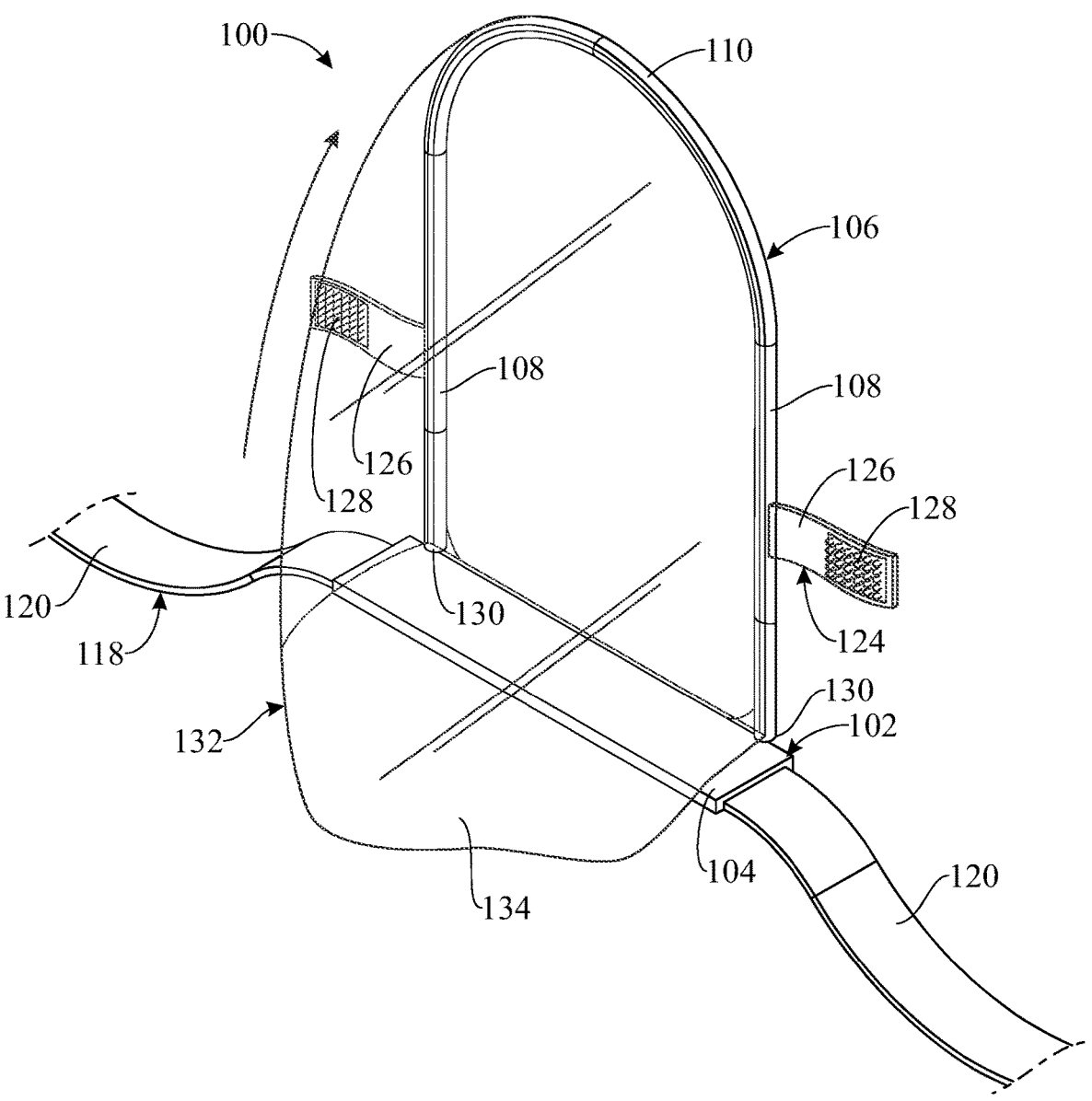
FIG. 3 presents a perspective view of the airway isolation drape assembly of FIG. 1 with the frame channel pivoted upwardly in a non-horizontal position with respect to the frame base of the drape frame preparatory to deployment of the drape over a subject (not shown)

In some embodiments, a frame channel 106 extends from the frame base 104. At least one hinge, pivotable connection, deformable connection, or other attachment enabling a pivoting movement along a horizontal axis, and hereinafter referred to generically as frame hinge 130, may pivotally attach the frame channel 106 to the frame base 104. The frame channel 106 is capable of pivoting from a horizontal position, in which the frame channel 106 may be arranged a flat, coplanar position with respect to the frame base 104, as illustrated in FIGS. 1 and 2, to a non-horizontal position in which the frame channel 106 is elevated at a nonzero angle with respect to the frame base 104, as illustrated in FIG. 3.

In some embodiments, the frame channel 106 can have a generally elongated, U-shaped configuration; however, alternative shapes are contemplated. In some embodiments, the frame channel 106 may include a pair of elongated, parallel, spaced-apart side channel segments 108 which extend from the frame base 104 in parallel, spaced-apart relationship to each other and in a longitudinal direction. An end channel segment 110 of the frame channel 106 may connect the side channel segments 108. In some embodiments, such as the present embodiment, the end channel segment 110 may be curved; alternative embodiments are contemplated in which the end channel segment 110 may have a different shape, such as but not limited to, straight. A frame opening 116 may be collectively formed by the frame base 104 and the side channel segments 108 and the end channel segment 110 of the frame channel 106.

A frame wire 114 may extend through the frame channel 106 of the drape frame 102. The frame wire 114 may include a metal, plastic and/or other material. In some embodiments, the frame wire 114 may be deformable. In some embodiments, the frame wire 114 may be elastically deformable. In other embodiments, the frame wire 114 may be plastically deformable.

Figure 7:
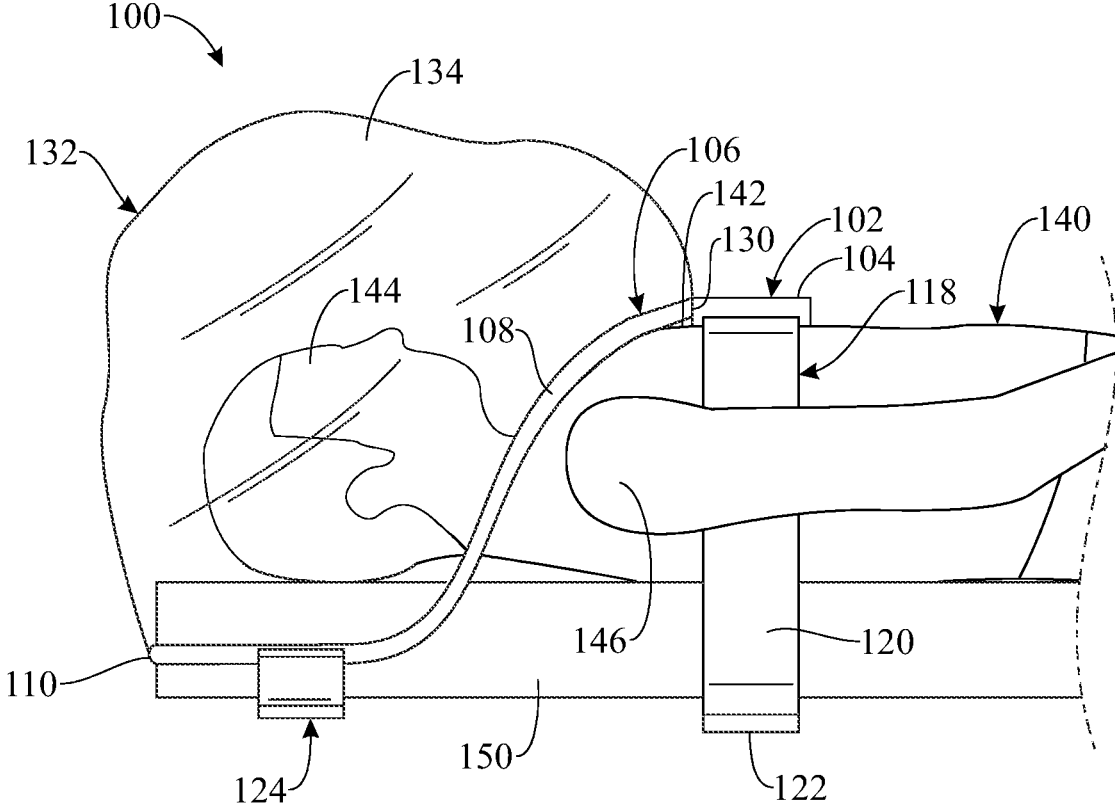
FIG. 7 presents a side view of the airway isolation drape assembly of FIG. 1 with the frame channel and drape deployed over the head of the subject.

In application of the drape assembly 100, the frame wire 114, particularly if plastically deformable, may enable the frame channel 106 of the drape frame 102 to conform to the chest 142 and shoulders 146 of the subject 140, as illustrated in FIG. 7 and will be hereinafter described. If elastically deformable, the frame wire 114 may recover an original shape, which may facilitate use of the drape assembly 100 in certain applications, such as when there is sufficient space available and/or there is a need for rapid deployment and placement of the drape assembly 100 to cover a subject, or to pivot the drape assembly 100 to a non-horizontal position away from the subject to uncover the subject's face or other area of the subject's body.

The drape assembly 100 may include at least one fastener configured to secure the drape assembly 100 to a subject support table, bed, or other structure (referred to herein as subject support structure or subject support surface 150). For example, the at least one fastener may include at least one base securement device 118 be provided on the frame base 104 of the drape frame 102 to facilitate securement of the frame base 104 to the subject support surface 150. In some embodiments, the base securement device 118 may include at least one base strap 120. For example, the at least one base strap 120 may include a pair of base straps 120 extending from opposite sides of the frame base 104.

At least one strap securing element 122 may be provided on at least one of the base straps 120 to facilitate securement of the base straps 120 to one another, to the subject support surface 150, to the subject, and/or to other structures, accessories or items (e.g., an accessory strap which interconnects the pair of base straps 120). In some embodiments, the strap securing element 122 may include at least one hook and loop fastener, for example and without limitation.

As illustrated in FIG. 2, in some embodiments, at least one frame base adhesive 112 may be provided on the underside of the frame base 104. The frame base adhesive 112 may, for instance, facilitate securement of the frame base 104 to the chest 142 or other body area of the subject 140, as will be hereinafter described.

At least one channel securement device 124 may be provided on the frame channel 106 of the drape frame 102.

The channel securement device 124 may facilitate securement of the frame channel 106 to the subject support surface 150. In some embodiments, the channel securement device 124 may include at least one channel strap 126. In some embodiments, the at least one channel strap 126 may include a pair of channel straps 126 extending from opposite sides of the frame channel 106.

At least one strap securing element 128 may be provided on the channel straps 126. In some embodiments, the strap securing element 128 may include at least one hook and loop fastener, for example and without limitation. In some embodiments, the strap securing element 128 may facilitate securement of the pair of channel straps 126 to one another, to the subject support surface 150, to the subject, and/or to other structures, accessories or items (e.g., an accessory strap which interconnects the pair of channel straps 126).

A drape 132 may extend between the side channel segments 108 and the end channel segment 110 in spanning relationship to the frame opening 116 of the frame channel 106. The drape 132 can span across the frame opening 116 collectively defined by the frame base 102 and the frame channel 106. The drape 132 may be fabricated as one or more sheets of transparent or translucent plastic and/or other flexible material. The sheets are preferably thin and lightweight, yet sufficiently protective, i.e. configured to filter harmful agents such as virus or bacteria. In some embodiments, the drape 132 includes two or more sheets, which are arranged in a stacked, parallel or consecutive relationship and are individually tearable or otherwise removable such that each sheet can be removed after use (such as when soiled), exposing the next available sheet.

The drape 132 may have a spanning portion 134 which may normally be disposed in a folded, stowage configuration (FIGS. 1 and 2) in the frame opening 116. The drape 132 may be selectively unfolded from the frame opening 116 to an extended, functional configuration (FIG. 3) to cover the face 144 of the subject 140, as illustrated in FIGS. 5 and 7. As illustrated in FIGS. 1 and 2, in some embodiments, the edge of the drape 132 may form a skirt portion 136 which extends from the spanning portion 134 beyond the frame channel 106 of the drape frame 102.

As illustrated in FIGS. 4-7, in application of the drape assembly 100, the subject 140 may recline on the subject support surface 150. As illustrated in FIG. 4, the drape assembly 100 may initially be placed over the abdomen and chest 142 of the subject 140. The frame base adhesive 112 (FIG. 2) may be applied to the chest 142 of the subject 140 to secure the frame base 104 of the drape frame 102 to the subject 140. The base securement device 118 may be deployed to secure the frame base 102 to the subject support surface 150.

Figure 6:
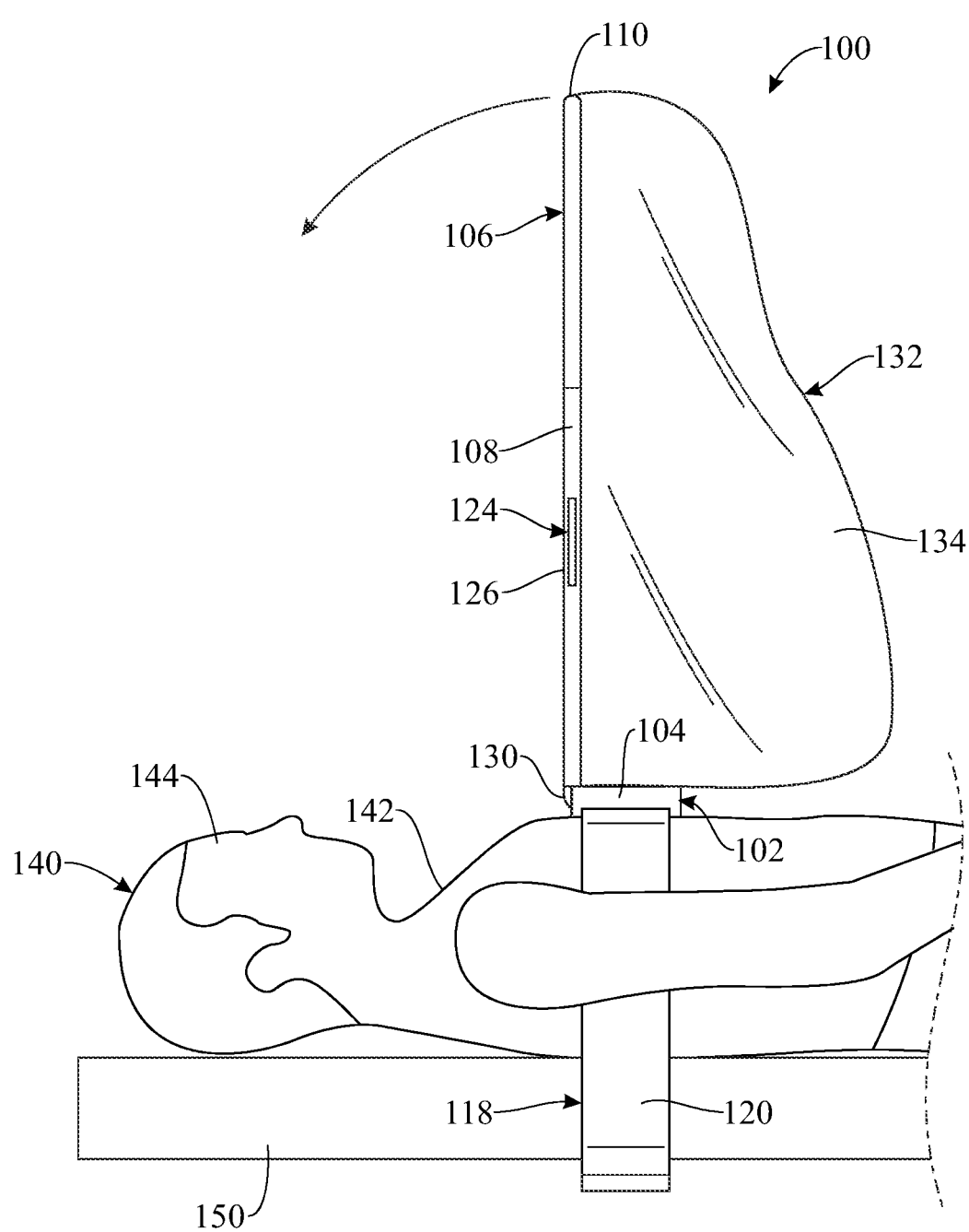
FIG. 6 presents a side view of the airway isolation drape assembly of FIG. 1 with the frame channel and drape oriented in a non-horizontal position preparatory to deployment of the frame channel and drape over the head of the subject.

As illustrated in FIG. 6, the frame channel 106 may be pivoted upwardly, via the frame hinged portions or hinges 130, from the horizontal, flat, coplanar position (FIG. 4) to the non-horizonal position. In some embodiments, the non-horizontal position is a raised, vertical, perpendicular position. The spanning portion 134 of the drape 132 may be unfolded from the frame opening 116 of the frame channel 106.

As illustrated in FIG. 7, the frame channel 106 may be pivoted down to the horizontal position against the chest 142 and shoulders 146 of the subject 140 as the spanning portion 134 of the drape 132 covers or encapsulates the chest 142, face 144 and shoulders 146 of the subject 140. As further illustrated in FIG. 7, the frame wire 114 (FIG. 1) in the frame channel 106 may enable the frame channel 106 to conform to the contour of the chest 142 and shoulders 146 of the subject 140. In some applications, the channel securement device 124 may be deployed to secure the frame channel 106 to the subject support surface 150.

With the drape 132 deployed in place over the face 144 off the subject 140, medical personnel (not illustrated) can access the nose and/or mouth for intubation and/or other purposes. A breathing apparatus, tool, device, or instrument (e.g., an oxygen tube) may be inserted through the drape 132 and into the nose and/or mouth of the subject 140 to facilitate breathing by the subject 140. The drape 132 may cover the chest 142 and face 144 of the subject 140 while preventing viruses, bacteria and/or other potentially harmful microorganisms which may be ejected from the mouth and/or nose of the subject 140 from contacting the medical personnel. In circumstances in which surgery is to be carried out above the subject's chest 142, the drape 132 may be moved up slightly. After use, the drape assembly 100 may be removed from the subject 140 and discarded.

Alternative embodiments of the invention are contemplated without departing from the scope of the present disclosure. For instance, the shape and size of the drape frame, drape and/or other components of the drape assembly 100 may vary, such as to accommodate subjects of various sizes or ages. In some embodiments, the drape frame and drape may be divided into more than one window or viewing area. In some embodiments, the drape may be entirely or partially opaque.

In some embodiments, the frame base may be jointly pivotable with the drape relative to the base straps or other fastener which secures the drape assembly to the subject support surface or other structure. In some embodiments, the frame base may be integrally formed with the base straps. For example, a strap may extend across the subject and optionally the subject support surface, and the drape (and accompanying frame wire and other elements, if present) may pivot relative to the strap.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An airway isolation drape comprising:
a drape frame including a frame base and a frame channel having a frame wire extending from the frame base, wherein the frame base and frame channel collectively define a frame opening; and
a drape including a spanning portion, the spanning portion configured to span across the frame opening of the drape frame;
wherein the frame channel of the drape frame is selectively positionable between a deployed configuration and a non-deployed configuration, the frame wire comprising a deformable material such that the frame channel conforms to an underlying anatomical surface when in the deployed configuration, and wherein the frame base is configured to remain stationary when the frame channel is in the deployed configuration, the deployed configuration defining a horizontal coplanar position of the frame channel with respect to the frame base.

2. The airway isolation drape of claim 1, further comprising:
a base securement device configured to secure the frame base to a surface.

3. The airway isolation drape of claim 2, wherein the base securement device includes:
a base strap extending from a side of the frame base; and
a base strap securing element configured to secure the base strap.

4. The airway isolation drape of claim 1, further comprising:
a channel securement device configured to secure the frame channel to a surface.

5. The airway isolation drape of claim 4, wherein the channel securement device includes:
a channel strap extending from a side of the frame channel; and
a channel strap securing element configured to secure the channel strap.

6. The airway isolation drape of claim 1, further comprising:
a frame hinge configured to couple the frame channel to the frame base and defining a horizontal axis, the frame hinge being configured to pivot the frame channel about the horizontal axis between the deployed configuration and the non-deployed configuration relative to the frame base.

7. The airway isolation drape of claim 1, wherein the drape frame is configured to be positioned in the non-deployed configuration, the non-deployed configuration defining a non-horizontal coplanar position of the frame channel with respect to the frame base.

8. The airway isolation drape of claim 1, wherein the drape includes a sheet of transparent or translucent material.

9. The airway isolation drape of claim 1, wherein the drape further comprises:
a skirt portion extending from the spanning portion beyond the frame channel of the drape frame.

10. A method, comprising:
providing an airway isolation drape, comprising:
a drape frame including a frame base and a frame channel having a frame wire and extending from the frame base, wherein the frame base and frame channel collectively define a frame opening; and
a drape including a spanning portion, the spanning portion configured to span across the frame opening of the drape frame;
wherein the frame channel of the drape frame is selectively positionable between a deployed configuration and a non-deployed configuration, the frame wire comprising a deformable material such that the frame channel conforms to an underlying anatomical surface when in the deployed configuration, and wherein the frame base is configured to remain stationary when the frame channel is in the deployed configuration, the deployed configuration defining a horizontal coplanar position of the frame channel with respect to the frame base;
securing the frame base to a subject and/or a support surface carrying the subject;
deploying the frame channel to the deployed configuration such that the drape frame and spanning portion of the drape encapsulate a head of the subject; and
securing the frame channel to the subject and/or a support surface carrying the subject.

11. The method of claim 10, further comprising:
a channel securement device configured to secure the frame channel to the subject and/or a support surface carrying the subject.

12. The method of claim 11, wherein the channel securement device includes:

a channel strap extending from a side of the frame channel; and a channel strap securing element configured to secure the channel strap.

13. The method of claim 12, further comprising:

securing the frame channel to the subject and/or a support surface carrying the subject by securing a first channel strap extending from a first side of the frame channel to a second channel strap extending from a second side of the frame channel.

14. The method of claim 10, wherein the airway isolation drape further includes:

a base securement device configured to secure the frame base to the subject and/or a support surface carrying the subject.

15. The method of claim 14, wherein the base securement device includes:

a base strap extending from a side of the frame base; and a base strap securing element configured to secure the base strap.

16. The method of claim 14, further comprising:

securing the frame base to the subject and/or a support surface carrying the subject by securing a first base strap extending from a first side of the frame base to a second base strap extending from a second side of the frame base.

17. The method of claim 10, wherein the airway isolation drape further comprises:

a frame hinge configured to couple the frame channel to the frame base and defining a horizontal axis, the frame hinge configured to pivot the frame channel about the horizontal axis between the deployed configuration and the non-deployed configuration relative to the frame base.

18. The method of claim 10, further comprising:

positioning the drape frame in the non-deployed configuration, the non-deployed configuration defining a non-horizontal coplanar position of the frame channel with respect to the frame base.

19. The method of claim 10, wherein the drape of the airway isolation drape further includes a sheet of transparent or translucent material.

20. The method of claim 10, wherein the drape of the airway isolation drape further includes:

a skirt portion extending from the spanning portion beyond the frame channel of the drape frame.

* * * * *